United States Patent [19]

Chang et al.

[11] Patent Number: 5,079,344
[45] Date of Patent: Jan. 7, 1992

[54] ANTIGENIC EPITOPES PRESENT ON MEMBRANE-BOUND BUT NOT SECRETED IGA

[75] Inventors: Tse-wen Chang; Nancy Chang, both of Houston, Tex.

[73] Assignee: Tanox Biosystems, Inc., Houston, Tex.

[21] Appl. No.: 369,479

[22] Filed: Jun. 21, 1989

[51] Int. Cl.$^5$ .......................... A61K 39/00; C12N 5/00
[52] U.S. Cl. ................................. 530/387; 435/240.27
[58] Field of Search ..................... 530/387; 435/240.27

[56] References Cited

FOREIGN PATENT DOCUMENTS 230883A 11/1985 Fed. Rep. of Germany .................. 435/240.27

OTHER PUBLICATIONS

Burnett, R. C. et al, "The IgA Heavy Chain Gene Family in Rabbitt: Cloning & Sequence Analysis of 13 C-α Genes", EMBO Journal 8:4041-47 (1989).
Robinson, E. A. et al, "Complete Amino Acid Sequence of a Mouse Immunoglobulin α Chain (MOPC 511)", PNAS 11:4909-13 (1980).
Osborne, B. A. et al, "Evolution of the Genus", Dialog Data Base File 5, Genetics 119:925-32 (1988).
Loghem, E. V. et al, "Allotypic and Isotypic Aspects of Human Immunoglobulin A", Molecular Immunology, vol. 20 (1983).
Kohler, G. et al, "Continuous Cultures of Fused Cells Secreting Antibody of Predefined Specificity", Nature 256:495-97 (1975).
Rogers, J. et al, "Two mRNAs with Different 3' Ends Encode Membrane-Bound and Secreted Forms of Immunoglobulin μ Chain", Cell 20:303-312 (1980).
Cooper, M. D. et al., "Effects of Anti-Ig Antibodies on the Development and Differentiation of B Cells", Immunological Rev. 52:29-53 (1980).
Komaromy, Michael et al., "The structure of the mouse immunoglobulin in $\gamma_3$ membrane gene segment", Nucleic Acids Research, 11:6775-6785 (1983).
Tyler, Brett M. et al, "mRNA for surface immunoglobulin γ chains encodes a highly conserved transmembrane sequence and a 28-residue intracellular domain", Proc. Natl. Sci. U.S.A., 79:2008-2012 (1982).
Vitetta; Ellen et al, "The Activation of Murine B Cells: The Role of Surface Immunoglobulins", Immunological Rev., 52:211-231 (1980).
Blattner et al, Nature, vol. 307, Feb. 2, 1984, pp. 417-422.
Kearney; J. F., Hybridomas and MAbs, Fundamental Immunology 1984, 751-766.
Word et al, The murine immunoglobulin α gene expresses multiple transcripts . . . , EMBO Jn. 1987, pp. 887-898.
Sitia et al, Memb. bound and secreted IgA contain struc. diff. α-chains, J. of Immunol. 1982, vol. 28, pp. 712-716.
Cushley et al., Nature, 298:77-79 (1982).

Primary Examiner—Margaret Moskowitz
Assistant Examiner—Lila Feisee
Attorney, Agent, or Firm—Eric P. Mirabel; Giulio A. DeConti, Jr.

[57] ABSTRACT

Antigenic epitopes associated with the extracellular segment of the domain which anchors immunoglobulins to the B cell membrane are disclosed. For IgA, the epitopes are present on IgA-bearing B cells but not the secreted, soluble form of IgA. The epitope can be exploited for therapy and prophylacsis. For example, antibodies specific for the epitopes associated with the anchor and peptide encompassing the epitope domain of IgA can be used to increase secretory IgA production for the purposes of treating patients susceptible with infectious diseases and IgE-mediated allergic diseases.

3 Claims, No Drawings

ANTIGENIC EPITOPES PRESENT ON MEMBRANE-BOUND BUT NOT SECRETED IGA

BACKGROUND

Numerous pathogenic microorganisms, such as bacteria and viruses, enter the human and animal bodies through the respiratory, gastrointestinal, and genitourinary tracts during air inhalation, food and liquid intake, and sexual contact. The immune system has evolved to meet the needs of defending against these pathogens by the development of secretory IgA antibodies. IgA is produced by plasma cells located along the mucosal linings of these various tracts that are exposed to the external environment. The $\alpha$ chain and light chain immunoglobulins produced by plasma cells combine with a secretory produced by the epithelial cells in the mucosal tissues, forming secretory IgA molecules that are secreted to the surface of mucosal layers. These IgA molecules bind to the invading pathogens and weaken their ability to penetrate the mucosal layer and to enter the inner tissue and blood stream of the hosts.

It is also well known that various allergic substances enter human and animal bodies through inhalation and food ingestion, causing immediate-type, antibody-mediated and delayed-type, cell-mediated hypersensitivities. The IgE-mediated reactions against pollens, animal danders, dust mites, and other allergic antigens cause common problems, such as hay fever (or allergic rhinitis) and extrinsic asthma among the sensitized individuals. In these allergic responses, the allergens enter the mucosal layers of the respiratory tracts and nasal linings and bind to allergen-specific IgE on the surface of mast cells. The cross-linking of IgE molecules by the allergens on the mast cell surface aggregates the underlying IgE Fc receptors, and trigger the release of histamine and other pharmacologic mediators, resulting in the various manifestations of allergic diseases. In the cell-mediated hypersensitivity, certain T helper cells responsible for delayed-type hypersensitivity are activated. These T cells recruit and activate macrophages, causing inflammatory symptoms.

In the two U.S. patent application Ser. Nos. 229,178, filed Aug. 5, 1988 and 272,243, filed Nov. 16, 1988, the discovery of antigenic epitopes unique to membrane-bound but not secreted immunoglobulins was described. Antibodies specific for these epitopes can be used for the elimination of B cells producing the immunoglobulins. In particular, antibodies specific for the antigenic locating in the transmembrane anchoring peptide of membrane-bound IgE can be used for the removal of IgE secreting B cells in patients suffering from IgE-mediated allergies.

Antibodies that belong to certain immunoglobulin classes and subclasses, such as murine $IgG_{2a}$ and $IgG_1$, and that have appropriately high affinity for binding to surface antigens of target cells, can cause the specific lysis of the target cells. However, not all antibodies specific for target cells will cause cytolysis. The antibodies specific for various isotypes of immunoglobulins (anti-Ig) antibodies) have been studied in numerous experiments to investigate the effects on B cells in vitro and in vivo. A broad range of effects, such as isotype switching, proliferation, increase or decrease of antibody production, have been reported. See Vitetta, E. D., et al., *Imunol. Rev.* 52:211-231 (1980); Cooper, M. D., et al., *Immunol. Rev.* 52:29-53 (1980). In numerous studies, polyclonal antibodies have been shown to induce B cells proliferation. See Sell, S. and Gell, P. G. H., *J. Exp. Med.* 122:423-44 (1965); Kishimoto, T., et al., *J. Immunol.* 115:1179-1184 (1975); Parker, D. C., *Nature* 258:361-363 (1975); Siekmann, D. G., et al., *J. Exp. Med.* 147:814-829; Pure, E. and Vitetta, E. S., *J. Immunol.* 125:1240-1242 (1980). Unlike antibody-dependent cellular cytotoxicity and complement-mediated cytolysis, this proliferative response does not seem to involve the Fc of the antibodies, because $F(ab')_2$ is more effective than whole antibody in inducing the proliferative effect. Vitetta, E. S. et al., *Immunol. Rev.* 52:211-231 (1980).

SUMMARY OF THE INVENTION

The inventions pertain to the various therapeutic applications of peptidic segments that are the extracellular portions of the transmembrane anchoring peptides of membrane-bound immunoglobulins. These peptide segments form entirely or partly the antigenic epitopes unique to membrane-bound but not secreted immunoglobulins. Synthetic peptides representing these regions of IgA can be conjugated to protein carriers and used to treat patients to modulate the synthesis of immunoglobulins, in particular, the increased synthesis of IgA. Antibodies specific for these antigenic epitopes, of certain immunoglobulin classes and subclasses, such as mouse $IgG_1$ or human $IgG_2$ or in the form of divalent antigen binding fragments such as $F(ab')_2$, can also be used to enhance IgA synthesis. Further, peptides representing the IgM or IgD, or antibody specific for these peptides, can be used to stimulate IgA production. These peptides and antibodies can be used alone, or combined with vaccines, or allergenic antigens, to increase IgA synthesis. The patients populations include those susceptible to infectious diseases and those affected by allergic diseases.

DETAILED DESCRIPTION OF THE INVENTION

1. Modulation of B Cell Activity by Antibodies Specific for Various Immunoglobulin Isotypes Owing mostly to the development of monoclonal antibody methodologies, the morphologically indistinguishable T lymphocytes are now known to contain functionally distinct subpopulations. Monoclonal antibodies specific for unique differentiation antigens of T cell subsets, such as CD3, CD4, CD8, etc., provide not only tools to identify the cells but also agents to modulate T cell activity in vitro and in vivo.

B lymphocytes produce five classes of immunoglobulins, which mediate different functions. IgM is most effective in complement fixation, IgG causes opsonization and cellular cytotoxicity and cross placenta, IgA functions on the mucosal surface and IgE mediates degranulation of mast cells and basophils. The function of IgD is still not well understood. These antibodies are present in the blood circulation, with IgG, IgA, and IgM accounting for as major serum components. In addition to secreting immunoglobulins, the B cells also express one or more isotypes of immunoglobulins on the cell surface at different stages of maturation. IgM and IgD are present on the surface of resting, uncommitted B cells, while each of all five classes of immunoglobulins may exist on late stage, mature B cells, which are committed to secrete the same isotypes of immunoglobulins as expressed on the cell surface. Teale, J. M., et al., *J. Immunol.* 126:1952-1957 (1981); Gathings, W. E., et al., *Immunol. Rev.* 57:107-126 (1981); Teale, J. M., *Fed. Proc.* 41:5-9 (1982).

Numerous investigators have contributed a large body of literature on the studies of effects of anti-Ig antibodies on the activity of B cells. In the volume of review articles, "Effects of anti-immunoglobulin sera on B lymphocyte function", *Immunol. Rev.* Vol. 52, ed. by Moller, G. (1980), it was clear that anti-Ig antibodies have broad ranges of effects on B cells. Among those effects, the proliferative activities on B cells and the production of IgM, IgG and IgA were most extensively studied using anti-IgM and Anti-IgD antibodies. Anti-IgM and Anti-IgD antibodies appear to be able to switch the uncommitted B cells to producers of IgG and IgA. The conclusive findings from these studies are that the effects of anti-Ig antibodies to stimulate B cell proliferation require the divalency of the antibodies and involve the cross-linking of the surface Ig. The effects do not require Fc portions of the antibodies and, in fact, the F(ab')$_2$ fragments appear to be more effective than whole IgG in stimulating B cell proliferation.

The effects of anti-Ig antibodies on B cell proliferation would seem highly desirable for modulating B cell activity in vivo for enhancing antibody production. However, these effects are hardly attainable because of the very large concentrations of IgG, IgM, and IgA antibodies in the circulation. When anti-Ig antibodies are administered in vivo, they will bind to the circulating Ig before they can bind to significant amounts to the surface Ig on B cells. The present invention pertains to the development of antibodies than can be used to react with membrane-bound immunglobulins to modulate B cell activity without reacting with secreted, circulating immunoglobulins.

2. IgA is Important for Immune Functions on Mucosal Surface

Some of the most common and serious infectious diseases, such as syphilis, AIDS, influenza, hepatitis B, are caused by pathogenic bacteria and viruses, that enter the human bodies through the respiratory, gastrointestinal, or genitourinary tracts. In much the same way that pathogenic microorganisms enter the airway of human respiratory system, the potentially allergic substances, such as tree, grass, or flower pollens, dust mites and fungal particles, animal danders, enter the human body.

The IgA antibody evolves for the defense at the mucosal surface against various foreign substances. IgA is synthesiszed by plasma cells found in higher densities near the linings of tracts that have exposure to the external environment. The IgA can bind to pathogenic mocroorganisms, weakening their ability to penetrate the mucosal layer to enter the inner tissue and blood stream. The IgA can also bind to allergenic substances, neutralizing or immobilizing the allergens to bind IgE or to activate T cells responsible for delayed-type hypersensitivity.

It has been found that individuals with deficiency of IgA production are more prone to various infectious diseases and have higher tendency to develop allergic diseases than those with normal IgA levels. These findings suggest that among those with susceptibility to contract infectious diseases and potential to develop allergic diseases, if the levels of either total IgA or antigen-specific IgA can be increased, the diseases may be prevented.

3. Anchoring Peptide Piece of B Cell Membrane-bound Immunoglobulins

B cells express on their surface antibody molecules, which serve as receptors for antigens during immunological induction. The membrane-bound immunoglobulins differ from the secretory immunoglobulins synthesized by the same cells in that they have extra peptidic pieces that anchor the immunoglobulin molecules onto the cell surface.

The amino acid sequence data of the eleven membrane-bound immunoglobulins from several species have been determined. See Word, C. J. et al., *EMBO J.* 2:887-898 (1983): Ishida, N. et al., *EMBO J.*, 1:1117-1123 (1982); Steen, M. L. et al., *J. Mol. Biol.*, 177:19-32 (1984); Rogers, J. et al., *Cell* 26:19-27 (1981); Yamawaki-Kataoka, Y. et al., *Proc. Natl. Acad. Sci., U.S.A.*, 79:2008-2012 (1982); Kamaromy, M. et al., *Nucleic Acids Res.*, 11:6775-6785 (1983); Rogers, J. et al., *Cell,* 20:303-312 (1980); Bernstein, K. E., *J. Immunol.* 132:490-495 (1984); Cheng, H. et al., *Nature,* 296:410-415 (1982). These sequences indicate certain common features of the plasma membrane bound peptidic piece. As shown in Table 1, the peptidic anchor piece has three segments which are distinguishable based upon their locations in relation to the plasma membrane. Even though these peptidic pieces are short, ranging from 41 to 72 amino acid residues, and have been referred to as the "membrane-bound domain", the peptides are not entirely in the membrane lipid bilayer. In fact, only 25 amino acid residues, largely hydrophobic residues and threonine and serine residues, located in the middle part of the peptides, are in the lipid bilayer. The C-terminal, hydrophilic segments of 3 to 28 amino acid residues are located on the cytoplasmic side of the membrane. The segments toward the N-terminus, which are connected to the third or fourth constant domains of the immunoglobulin heavy chains (CH$_3$ or CH$_4$) are very hydrophilic and are on the extracellular side of the plasma membrane.

TABLE 1

| Key features and properties of peptidic segments unique to membrane bound immunoglobulins on B cells. | | | |
|---|---|---|---|
| | First segment | Middle segment | Last segment | Total |
| Immunoglobulin Class/Subclass | Length # Amino acid residues | | |
| Mouse IgA | 26 | 25 | 14 | 65 |
| Mouse IgE | 19 | 25 | 28 | 72 |
| Rat IgE | 19 | 25 | 28 | 72 |
| Mouse IgG$_1$ | 18 | 25 | 28 | 71 |
| Mouse IgG$_{2a}$ | 18 | 25 | 28 | 71 |
| Mouse IgG$_{2b}$ | 18 | 25 | 28 | 71 |
| Mouse IgG$_3$ | 18 | 25 | 28 | 71 |
| Mouse IgM | 13 | 25 | 3 | 41 |
| Rabbit IgM | 13 | 25 | 3 | 41 |
| Human IgD | 27 | 25 | 3 | 55 |
| Mouse IgD | 26 | 25 | 3 | 54 |
| Properties | Hydrophilic Highly acidic | Hydrophobic No charged residues | Hydrophilic |
| Physical Location | On exterior surface | In membrane lipid bilayer | On cytoplasmic surface |
| Abbreviated Symbols | mb/ec segment | mb/tm segment | mb/ic segment |

*mb for membrane-bound; ec for extracellular; tm for transmembrane; and ic for intracellular.

The shortest length of the extracellular segment of the membrane-bound pieces of the immunoglobulins (designated mb/ec segments) has 13 amino acid residues (mouse and rabbit μ chains). See Table 2. The mb/ec segments of all immunoglobulins contain high proportions of charged amino acid residues, almost entirely acidic residues. The proportions of charged amino acid residues and polar hydrophilic residues account for very high percentages of the amino acid composition of the mb/ec segment (Table 3). These parameters indicate that all the mb/ec segments are exposed and long enough to be accessible by antibodies. The heavy chains evolved before the various mammals species, mice, rats, and humans evolved. Thus, among the various mb/ec segments that have been determined, it is probably the murine α.mb/ec that the human α.mb/ec, which sequence has not yet been reported, will be most related. The murine α.mb/ec has 26 amino acid residues, among them 5 Glu and 2 Asp residues. These data also provide support that human αmb/ec segment is exposed and accessible to antibodies.

by Invitrogen (San Diego, Calif.). Stepwisw detailed instruction manual is provided for RNA isolation from cells, reverse transcription, second strand synthesis, linker ligation, agarose gel sizing of cDNA, electroelution to purify cDNA, vector ligation, and transformation of E. coli. The vector used in this library is pCDM8.

In the screening of the cDNA library for clones containing the αmb/ec segment, several probes can be used. The library can be screened with a DNA probe, which is a 30 base long oligonucleotide, representing a segment located in the CH3 domain of the α chain--GCGAGAAGTA.CCTGACTTGG.-GCATCCCGGC. The positive clones, which include both secreted and membrane-bound forms can be distinguished by using additional probes. A probe based on

TABLE 2

The amino acid sequences of the exterior portion of peptidic segments unique to membrane-bound immunoglobulins (mg/ec segments).

| | Mb/ec segment | | | | |
|---|---|---|---|---|---|
| | 26 | 21 | 16 | 11 | 6 | 1 |
| Mouse IgA | E. | RQEPL. | SYVLL. | DQSQD. | ILEEE. | APGAS |
| Mouse IgE | | . | ELDI. | QDLCI. | EEVEG. | EELEE |
| Rat IgE | | | ELDI. | QDLCT. | EEVEG. | EELEE |
| Mouse IgG$_1$ | | | GLQ. | LDETC. | AEAQD. | GELDG |
| Mouse IgG$_{2a}$ | | | GLD. | LDDVC. | AEAQD. | GELDG |
| Mouse IgG$_{2b}$ | | | GLD. | LDDIC. | AEAKD. | GELDG |
| Mouse IgG$_3$ | | | ELE. | LNGTC. | AEAQD. | GELDG |
| Mouse IgM | | | | EGE. | VNAEE. | EGFEN |
| Rabbit IgM | | | | EGE. | VNAEE. | EGFEN |
| Human IgD | YL. | AMTPL. | IPQSK. | DENSD. | DYTTF. | DDVGS |
| Mouse IgD | I. | VNTIQ. | HSCIM. | DEQSD. | SYMDL. | EEENG |

TABLE 3

Composition of charged amino acid residues and polar, hydrophilic amino acid residues in the exterior portion of peptidic segments unique to membrane-bound immunoglobulins (mb/ec segments).

| | TOTAL | Acidic residues | Basic residues | Polar residues | Total hydrophilic residues | Proportion of hydro philic residues |
|---|---|---|---|---|---|---|
| | # Amino acid residues | | | | | % |
| Mouse IgA | 26 | 7 | 1 | 7 | 15 | 58 |
| Mouse IgE | 19 | 10 | 0 | 2 | 12 | 63 |
| Rat IgE | 19 | 10 | 0 | 2 | 12 | 63 |
| Mouse IgG$_1$ | 18 | 6 | 0 | 4 | 10 | 56 |
| Mouse IgG$_{2a}$ | 18 | 7 | 0 | 2 | 9 | 50 |
| Mouse IgG$_{2b}$ | 18 | 7 | 1 | 1 | 9 | 50 |
| Mouse IgG$_3$ | 18 | 6 | 0 | 4 | 10 | 56 |
| Mouse IgM | 13 | 6 | 0 | 2 | 8 | 61 |
| Rabbit IgM | 13 | 6 | 0 | 1 | 7 | 54 |
| Human IgD | 27 | 6 | 1 | 8 | 15 | 56 |
| Mouse IgD | 26 | 7 | 0.5 | 9 | 16.5 | 63 |

Acidic residues: E (Glu), D (Asp)
Basic residues: K (Lys), R (Arg), H (His); His is partially charged.
Polar residues: S (Ser), T (Thr), C (Cys), Q (Gln), N (Asn)

4. Determining the amino acid sequence of mb/ec segment of human IgA (α.mb/ec segment)

A number of well established procedures can be applied to determine the DNA sequence corresponding to the human αmb/ec segment. In one approach the starting point is the mRNA preparation of a human myeloma cell line which express IgA on the surface. DAKIKI cell line (American Type Collection, TIB#206) can be employed for this purpose. With the mRNA preparation, one can establish a cDNA library employing cloning vector with λ phage or plasmids. A preferred method for constructing the cDNA library is with the cDNA Library Construction System Kit - Librarian I developed I developed and commercialized the finding that the transmembrane segment of the membrane-bound domain (mb/tm segment) is very conserved among all the immunoglobulin genes so far sequenced can be used. There is a segment of peptide and its corresponding coding DNA within this mb/tm segment, that is nearly identical among all immunoglobulins. As shown in Table 4, the consensus DNA sequence with the eight combinations will be used.

TABLE 4

A conserved region in the transmembrane portion of the peptidic segment of the membrane-bound immunoglobulins (in mb/tm segment.

|  | 1<br>Leu. | 2<br>Phe. | 3<br>Leu. | 4<br>Leu. | 5<br>Ser. |
|---|---|---|---|---|---|
| Mouse IgA | CTC. | TTC. | CTA. | CTG. | AG |
| Mouse IgE | CTG. | TTC. | CTG. | CTC. | AG |
| Rat IgE | CTG. | TTC. | CRG. | CTC. | AG |
| Mouse IgG$_1$ | CTC. | TTC. | CTG. | CTC. | AG |
| Mouse IgG$_{2a}$ | CTC. | TTC. | CTG. | CTC. | AG |
| Mouse IgG$_{2b}$ | CTC. | TTC. | CTG. | CTC. | AG |
| Mouse IgG$_3$ | CTC. | TTC. | CTG. | CTC. | AG |
| Mouse IgM | CTC. | TTC. | CTC. | CTG. | AG |
| Rabbit IgM | CTG. | TTC. | CTG. | CTG. | AG |
| Human IgD* | CTC. | TTC. | ATC. | CTC. | AC |
| Mouse IgD* | CTC.<br>C | TTC. | CTG.<br>G | CTC.<br>C | AC |
| Consensus sequence (Probe c) | CT.<br>G | TTC. | CT.<br>C | CT.<br>G | AG |

*Human and mouse IgD's have Thr (ACXO in the 5th amino acid residue; human IgD also has Ile (ATC) in the 3rd amino acid residue. These are the variations not covered by the consensus sequence.

An alternative to the conventional approach of establishing cDNA library and screening the clones representing the cellular mRNA species is to amplify the mRNA to produce high proportions of their corresponding DNA. The resulting DNA can then be purified by gel electrophoresis and then subjected to sequence analysis. The methodology, referred to as polymerase chain reaction (PCR) amplification, has been established in the past few years and complete system including reagents and equipments have been commercialized. One preferred system is provided by Perkin Elmer Cetus (Norwalk, Conn.). The reagents kit is the GeneAmp DNA Amplification Reagent Kit and the equipment is the DNA Thermal Cycler.

Some of the specific reagents used in this approach are the same as used for the cDNA library cloning. Since no sequence in the membrane-bound segment of the human $\alpha$ chain has been determined, the strategy si to amplify both the secreted and membrane-bound forms of $\alpha$ chains by using pokly dT and the 30-mer oligonucleotide discussed above as primers. The two oligomers used in the cDNA cloning can also be used as primers in the PCR procedure.

Another approach of obtaining a DNA clone containing genes encoding the membrane-bound segments is to screen human genomic DNA library. Human genomic DNA library is readily available. A preferred source is the library constructed using human lung fibroblast WI38 cells provided by Stratogene (La Jolla, Calif.). The genes are in λ vector and the inserted DNA have average sizes of 15 K bp. Identification of the clones can be achieved by hybridization with the loigmoer probe of 30 bases used in cDNA cloning. The gene segment corresponding to the membrane bound can be determined by sequencing the nucleotide bases downstream. According to the genomic structure of all the immunoglobulins known, the membrane exon is within two to three thousand base pairs apart from the CH3 region.

5. Developing Antibodies to mb/ec Segment

The $\alpha$.mb/ec peptide can be used in the immunization of animals to prepare polyclonal and monoclonal antibodies. They can also be used to screen for specific monoclonal antibodies or characterize specific polyclonal antibodies. They can also be used to purify monoclonal and polyclonal antibodies.

In the process of preparing for monoclonal antibodies specific for $\alpha$.mb/ec peptide, it is not necessary to use the $\alpha$.mb/ec peptide in both immunization and antibody identification. For example, in immunizing mice for preparing immune spleen cells for fusion with myeloma cells, the immunogen may be the membrane-bound IgA isolated from plasma membrane of IgA-bearing myeloma cells, such as DAKIKI lymphoblastoid cells. The immunogen may also be the IgA-bearing myeloma cells.

For using the synthetic $\alpha$.mb/ec peptide for immunogen, it is more effective to conjugate the peptide to a protein carrier. A preferred protein carrier is keyhole lympit hemocyanin (KLH). If the peptidic segment lacks a Lys residue or if the Lys residue is in the middle part of the segment, it is desirable to add a Lys residue at the C-terminal end. Because the N-terminus already has an $\alpha$-amino group, the modified synthetic peptidic will have two amino groups for linking.

Multiple molecules of peptides can be conjugated to each molecule of the carrier protein. With KLH, a preferred molar ratio for peptide/KLH is 10. The method of conjugation is very well established. Cross-linkers such as glutaldehyde or bis (sulfoscinimidyl) suberate or disulfosuccinimidyl tartarate (Catalogue #21579, 20591 Pierce Chemical Co., Rockford, Ill.) have been used. A preferred cross-linker is the gluteraldehyde.

The immunogen, such as the KLH conjugate, can be used to immunize rabbits, goats, rats, or mice to prepare polyclonal antibodies specific for the $\alpha$.mb/ec peptide. Lympocytes from the spleen or lymph nodes of immune mice and rats can also be taken to prepare hybridomas secreting monoclonal antibodies specific for the $\alpha$.mb/ec peptide. A preferred protocol to prepare the monoclonal antibodies is to fuse immune spleen cells of mice with non-secreting mouse myeloma cells, such as NS-1 or SP2/0 cells using polyethylene glycol.

For optimal immunization of mice, 50 μg of the peptide-KLH conjugate in complete Fruend adjuvant is injected subcutaneously into each mouse for priming. Two and four weeks later, same amounts of antigen is given s.c. in incomplete Fruend adjuvant. At about the six week time point, the fourth antigen injection is given i.p. in saline. Mice are sacrificed 4 days after the last injection and the spleens are taken for preparing single cell suspension for fusion with myeloma cells. Similar protocol can also be used for immunization with purified native human membrane-bound IgA (having attached membrane anchor domain) isolated from the plasma membrane of IgA-bearing human myeloma cells, such as DAKIKI lymphoblasted cells. When human IgA-bearing cells are used as the immunogen, $1 \times 10^7$ cells are injected i.p. with two week intervals.

The fusion procedure with polyethylene glycol and other various procedures concerning cloning and hybridoma culturing have been well established and the preferred protocol is the same as described by Hudson, L. and Hay. F. C. (Practical Immunology, 2nd edition, pp. 303-313, 1980, Blackwell Publishing Co., Boston).

The screening of hybridomas for monoclonal antibodies or the identification of polyclonal antibodies with $\alpha$.mb/ec peptide can be performed with enzyme linked immunosorbent assays (ELISA) using the synthetic $\alpha$.mb/ec peptide as the solid phase antigen. An alternative solid phase antigen is the conjugate of $\alpha$.mb- /ec peptide with a different carrier protein such as bovine serum albumin different from that used in immunogen. Further characterization of the monoclonal and polyclonal antibodies are shown in Table 5. The assays employed in these studies are also indicated. The assays have been described in detail in the U.S. patent application Ser. No. 226,421, filed July 29, 1988, and U.S. patent application Ser. No. 140,036, filed Dec. 31, 1987, the teachings of which are incorporated by reference herein.

TABLE 5

The reactivity of antibodies specific for α.mb/ec peptide with different IgA-containing targets.

| | Reactivity | Assays |
|---|---|---|
| Synthetic α.mb/ec peptide | + | ELISA |
| Soluble IgA | − | ELISA |
| DAKIKI myeloma cells | + | Immunofluorescence staining |
| IgA-bearing B cells | + | Immunofluorescence staining |
| Cells not expressing surface IgA | − | Immunofluorescence staining |

6. Experiments with Animal Models

The substances and methods are tested on animal model systems. A number of experiments are designed to investigate whether peptides representing ec/mb segments of various immunoglobulins and the antibodies for these antigenic epitopes will enhance the production of IgM, IgG, IgA, etc. in the animals. The peptides and antibodies relating to a particular isotype may have effects on the synthesis of several isotypes and subclasses. In the discussion below, we will primarily focus on peptides and antibodies relating to α.ec/mb segment. The purposes of the animal studies are to investigate;
a) Do the peptides and antibodies enhance antibody production?
b) Do the peptides and antibodies enhance secretory IgA production in the mucosal surface?
c) Can the peptides and antibodies be used prophylactically in preventing from infectious diseases?
e) Can the peptides and antibodies be used in patients with immunodeficiency diseases?
f) Can the peptides and antibodies be used in patients to prevent from or alleviate symptoms of allergic diseases?

Two of the most relevant systems are the following.

A. Primate model

The monoclonal antibodies specific for human α.mb/ec peptide and their related substances of this invention are tested to determine whether they react with IgA-bearing cells of rhesus monkeys.

A small portion of rhesus monkeys, which have been infected with the nematode, *Ascaris suum*, develop sensitivity to extract of ascaris. When these sensitive monkeys are given spray containing ascaris antigen, they develop breathing problems resembling asthma. Patterson, R., *J. Clini. Invest.* 57:586–593 (1976).

The various compositions of this invention can be examined in the asthma/rhesus monkey model system. The ascaris sensitive monkeys are given the experimental treatment or control treatment and measurements are made to determine:
a) Does the asthma symptoms upon ascaris challenge decline?
b) Does the circulating IgA increase?
c) Does secretary IgA increase in pulmonary lavage?
d) Does Ascaris antigen specific IgA increase?
e) Does the circulating IgA-bearing B cells increase?

B. Mouse model system

The α.mb/ec segment of mouse has already been sequenced. Word, C. J. et al., *EMBO J.* 2:887–898 (1983). The 26 amino acid residue peptide is
Glu-Arg-Gln-Glu-Pro-Leu-Ser-Tyr-Val-Leu-Leu-Asp-Gln-Ser-Gln-Asp-Ile-Leu-Glu-Glu-Glu-Ala-Pro-Gly-Ala-Ser.

The peptide is synthesized in several forms, including one that has extra Leu-Lys residues at the C-terminus.

The peptide and its KLH conjugate are used as antigens to immunize rabbits and goats. The antisera are collected. The antigen-specific antibodies are purified using column of Sepharose 4B conjugated with the peptide (with Leu-Lys addition) or with peptide linked to bovine serum albumin. Normal mice are injected i.v. or i.p. with the purified antibodies or their related substances. The mice may also be given αec/mb peptide-conjugated with LKH. They can also be immunized with a viral antigen, such as from rotavirus, combined with antibody or peptide treatment. The questions to be investigated are:
(a) Does the total IgA in circulation increase?
(b) Does total secretory IgA increase in the intestinal lumen?
(c) Does antigen-specific IgA increase?
(d) Does the number of IgA-bearing B cells in the spleen and Peyer's patches increase?
(e) Can the mice resist better the challenge with live virus?

7. Application of α.ec/mb Peptide and Antibodies Specific for this Epitope in Infectious Diseases, Allergies, and Immunodeficiency Diseases The α.ec/mb peptide and antibodies specific for α.mb/ec epitopes can be used to increase total IgA, secretory IgA, or antigen-specific IgA in humans or other animals (e.g. dogs, cats and horses). The antibodies can be used therapeutically and prophylactically in several ways.

A. Antibodies specific for IgA-bearing cells

Antibodies of certain IgG subclasses, such as mouse $IgG_1$ and human $IgG_2$ and $IgG_4$, or F(ab')2 fragments may be used to achieve the purposes of enhancing antibody production. The antibodies can be administered as free antibodies to patients in amounts sufficient to induce proliferation of IgA-bearing B cells and, hence increase IgA production.

The antibodies can also be administered nasally. On the lining of nasal channel and respiratory tract are areas in which IgA-producing B cells reside in denser populations. It is possible that a nasal route of administration (e.g. by nasal spray) may be used to deliver relatively high concentrations of antibodies into these areas and thus to achieve speedier and more effective results. The antibodies can also be administered ocularly.

For therapeutic uses in humans, either human or chimeric (or "near-human"0 antibodies are preferred. Chimeric antibodies comprise a variable or antigen binding (hypervariable or complementarity determining) region derived from an animal antibody and the remaining regions derived from a human antibody. Methods for producing chimeric (e.g. murine/human) antibodies are well established. Chimeric antibodies can be produced in large quantities and they are less immunogenic in humans than nonhuman antibodies. Consequently, they are better suited for in vivo administration, especially when repeated or long term administration is necessary. Antibody fragments of the chimeric antibodies can also be used.

Immunotherapies employing the antibodies of this invention may be used in combination with conventional vaccination and desensitization immunotherapy. For example, desensitization with allergen may be performed in conjunction with the administration of anti-α.mb/ec antibodies.

B. α.mb/ec Peptide Analogues and Active Immunization Against α.mb/ec Epitope

Even though human α.mb/ec peptide is probably not immunogenic in humans, peptide with the same sequence and amino acid substitutions can be linked to carrier proteins, such as hepatitis B surface antigen or core antigen, and become immunogenic and capable to induce antibodies that cross react with authentic αmb/ec epitope. The α.mb/ec peptide analogues can be administered to patients susceptible to infectious diseases or IgE-mediated allergies. The antibodies induced by this active immunization can achieve the functions as the antibodies described in section A.

C. Antiidiotypic Antibodies and Methods of Active Immunization Against α.mb/ec Epitope The α.mb/ec-specific monoclonal antibodies described thus far can be used to generate parotype-specific, anti-idiotypic antibodies which offer another mode of stimulating IgA production. Antibodies against the parotype of the α.mb/ec-specific antibodies conformationally resemble the epitope for which the anti-IgA antibody is specific, that is, they resemble an α.mb/ec epitope. These anti-idiotypic antibodies can be used to actively immunize against α.mb/ec and induce the endogenous formation of antibodies against the α.mb/ec epitope. The induced antibodies will mediate the various prophylactic and therapeutical effects of α.mb/ec-specific antibodies.

Because anα.mb/ec epitope is a "self-molecule", it is not immunogenic. However, active immunization against it may be achieved by using the parotope-specific antibodies of this invention. The parotype-specific antibody shares conformational resemblance with the antigen—the α.mb/ec epitope—which can elicit immune response in humans against the epitope.

Paratope-specific, anti-idiotypic antibodies are administered to a patient in an immunogenic amount to induce the formation of α.mb/ec antibodies. The anti-idiotypic antibodies are preferably administered as chimeric antibodies. They may also be given as antibody fragments (which also may be chimeric in nature).

8. Diagnostic Uses

Antibodies against α.mb/ec epitopes can be used to identify and enumerate IgA-bearing lymphocytes in mixed leukocyte populations. For this purpose, antibodies can be used in standard assay formats for determining cell surface antigens. In general, the antibody is contacted with a sample of the leukocytes to be tested under conditions which allow the antibody to bind IgA-bearing cells in the sample. The cells are then examined for binding of antibody. This can be accomplished by conventional cell staining procedures. For example, a fluorescently labeled second antobody can be used to detect binding of the anti-IgA antibody.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A monoclonal antibody, or fragment thereof, which binds specifically to human IgA on the surface of B cells but does not bind to secreted, soluble IgA.

2. A hybridoma cell line which produces a monoclonal antibody which binds to human IgA on the surface of B-cells but does not bind to secreted, soluble IgA.

3. A cell line of claim 2, which is a murine hybridoma.